US012663772B2

(12) United States Patent
White et al.

(10) Patent No.: US 12,663,772 B2
(45) Date of Patent: Jun. 23, 2026

(54) SYSTEM AND METHOD FOR CONTROLLING A BEDROOM ENVIRONMENT CONTROL USING A SLEEP TRACKING SYSTEM

(71) Applicant: Innovative Health Monitoring LLC, Stamford, CT (US)

(72) Inventors: Eric Gregory White, Tinton Falls, NJ (US); David Robert Abrams, Aberdeen, NJ (US)

(73) Assignee: Innovative Health Monitoring LLC, Stamford, CT (US)

( * ) Notice: Subject to any disclaimer, the term of this patent is extended or adjusted under 35 U.S.C. 154(b) by 498 days.

(21) Appl. No.: 17/902,566

(22) Filed: Sep. 2, 2022

(65) Prior Publication Data

US 2023/0032770 A1 Feb. 2, 2023

Related U.S. Application Data

(63) Continuation-in-part of application No. 17/887,426, filed on Aug. 13, 2022, which is a continuation-in-part of application No. 17/872,952, filed on Jul. 25, 2022.

(60) Provisional application No. 63/241,539, filed on Sep. 8, 2021, provisional application No. 63/233,388, filed on Aug. 16, 2021, provisional application No. 63/226,703, filed on Jul. 28, 2021.

(51) Int. Cl.
    *G05B 19/042*  (2006.01)
    *A61M 21/02*  (2006.01)

(52) U.S. Cl.
    CPC .......... *G05B 19/042* (2013.01); *A61M 21/02* (2013.01); *A61M 2205/3303* (2013.01); *A61M 2205/3313* (2013.01); *G05B 2219/2614* (2013.01)

(58) Field of Classification Search
    CPC ......... G05B 19/042; G05B 2219/2614; A61M 21/02; A61M 2205/3303; A61M 2205/3313
    See application file for complete search history.

(56) References Cited

U.S. PATENT DOCUMENTS

| | | | | |
|---|---|---|---|---|
| 10,376,670 B2 * | 8/2019 | Shouldice | ............... | G10L 15/26 |
| 10,709,335 B2 * | 7/2020 | Matsuoka | .......... | G08B 21/0208 |
| 11,364,362 B2 * | 6/2022 | Shouldice | .......... | A61B 5/14865 |

(Continued)

OTHER PUBLICATIONS

International Search Report and Written Opinion for PCT Application PCT/US2022/038214, mailed on Oct. 12, 2022.

(Continued)

*Primary Examiner* — Shirley X Jian
(74) *Attorney, Agent, or Firm* — Greenberg Traurig, LLP

(57) ABSTRACT

A method and system that is integrated in order to provide an automated control system for the user, which provides messaging to bedroom environmental control systems as a function of the status of the user's sleep state is disclosed herein. The system comprises a sleep monitoring sub-system and a bedroom environmental control sub-system. The sleep monitoring sub-system is configured to transmit the subject's sleep progression data to an interface for the bedroom environmental control system. The bedroom environmental control system is configured to modify a bedroom environment based on the subject's sleep progression data.

12 Claims, 5 Drawing Sheets

(56)　　　　　References Cited

U.S. PATENT DOCUMENTS

| 11,648,373 | B2 * | 5/2023 | Shouldice | A61B 5/486 |
| | | | | 600/26 |
| 11,986,600 | B2 * | 5/2024 | Shouldice | A61B 5/14865 |
| 2008/0045847 | A1 | 2/2008 | Farag et al. | |
| 2008/0142713 | A1 | 6/2008 | Breed et al. | |
| 2009/0203972 | A1 * | 8/2009 | Heneghan | A61B 5/0507 |
| | | | | 600/301 |
| 2013/0310662 | A1 * | 11/2013 | Tsutsumi | A61B 5/4812 |
| | | | | 600/595 |
| 2014/0023235 | A1 | 1/2014 | Cennini et al. | |
| 2014/0058256 | A1 | 2/2014 | De Jong | |
| 2014/0326888 | A1 | 11/2014 | Barlow et al. | |
| 2015/0078642 | A1 | 3/2015 | Fang | |
| 2015/0094914 | A1 * | 4/2015 | Abreu | B60H 1/00742 |
| | | | | 701/1 |
| 2015/0105976 | A1 * | 4/2015 | Shikii | B60W 40/08 |
| | | | | 701/36 |
| 2016/0151603 | A1 * | 6/2016 | Shouldice | A61B 5/486 |
| | | | | 600/26 |
| 2017/0303830 | A1 | 10/2017 | Klein et al. | |
| 2017/0319114 | A1 | 11/2017 | Kaestle | |
| 2018/0053393 | A1 | 2/2018 | White et al. | |
| 2018/0168020 | A1 * | 6/2018 | Casey | H05B 47/19 |
| 2018/0263502 | A1 | 9/2018 | Lin et al. | |
| 2018/0279885 | A1 | 10/2018 | Bulut | |
| 2019/0000391 | A1 | 1/2019 | De Haan et al. | |
| 2019/0139389 | A1 | 5/2019 | White et al. | |
| 2019/0200872 | A1 * | 7/2019 | Matsuoka | G08B 21/0202 |
| 2019/0205655 | A1 * | 7/2019 | Matsuoka | G06V 40/161 |
| 2019/0206062 | A1 * | 7/2019 | Matsuoka | A61B 5/1128 |
| 2020/0022628 | A1 | 1/2020 | Tao et al. | |
| 2020/0265602 | A1 | 8/2020 | Ostadabbas et al. | |
| 2020/0345274 | A1 | 11/2020 | Ghoshal et al. | |
| 2021/0181307 | A1 | 6/2021 | Ni et al. | |
| 2022/0386947 | A1 * | 12/2022 | Garcia Molina | A61B 5/7267 |

OTHER PUBLICATIONS

International Search Report and Written Opinion for PCT Application PCT/US2022/040235, mailed on Nov. 3, 2022.
International Search Report and Written Opinion for PCT Application PCT/US2022/042515, mailed on Jan. 4, 2023.
International Search Report and Written Opinion for PCT Application PCT/US2022/050257, mailed on Feb. 28, 2023.

* cited by examiner

90

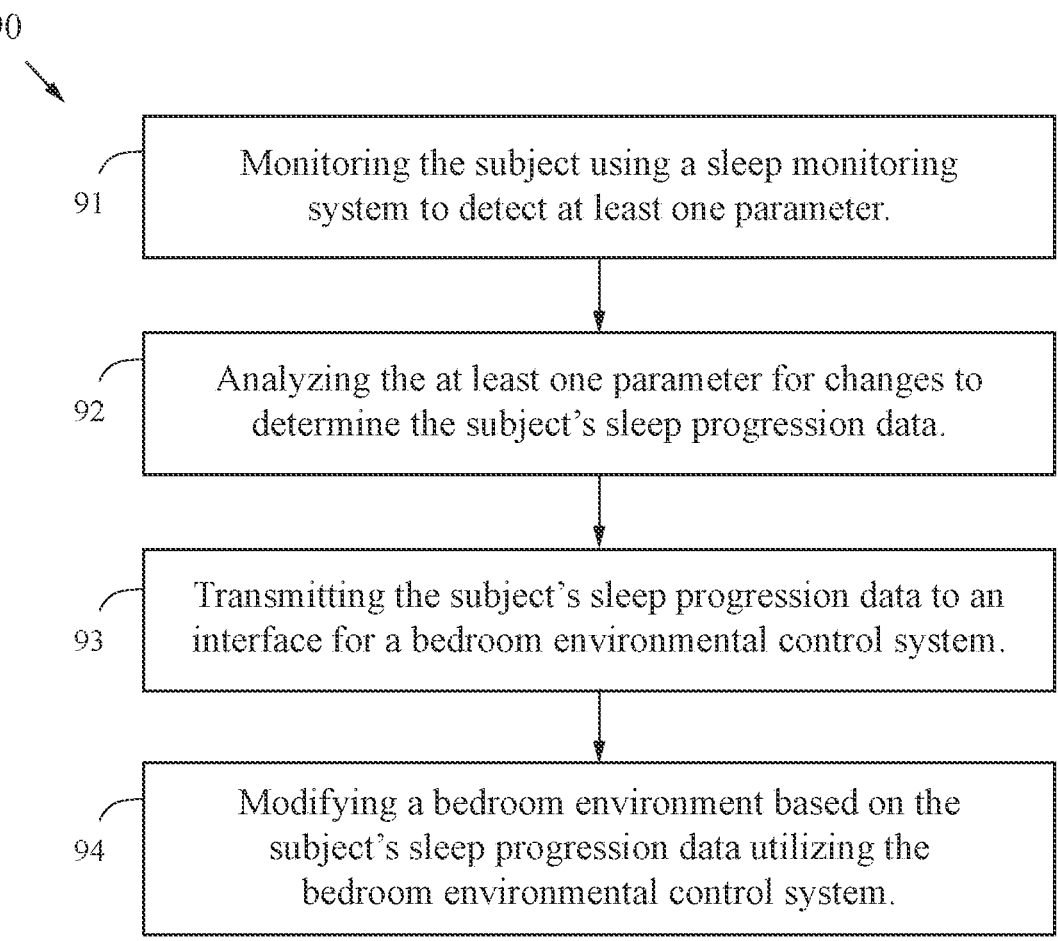

Monitoring the subject using a sleep monitoring
system to detect at least one parameter.

91

Analyzing the at least one parameter for changes to
determine the subject's sleep progression data.

92

Transmitting the subject's sleep progression data to an
interface for a bedroom environmental control system.

93

Modifying a bedroom environment based on the
subject's sleep progression data utilizing the
bedroom environmental control system.

SYSTEM AND METHOD FOR CONTROLLING A BEDROOM ENVIRONMENT CONTROL USING A SLEEP TRACKING SYSTEM

CROSS REFERENCES TO RELATED APPLICATIONS

The Present application claims priority to U.S. Provisional Patent Application No. 63/241,539, filed on Sep. 8, 2021, and the Present application is a continuation-in-part application of U.S. patent application Ser. No. 17/887,426, filed on Aug. 13, 2022, which claims priority to U.S. Provisional Patent Application No. 63/233,388 filed on Aug. 16, 2021, and is a continuation-in-part application of U.S. patent application Ser. No. 17/872,952, filed on Jul. 25, 2022, which claims priority to U.S. Provisional Patent Application No. 63/226,703, filed on Jul. 28, 2021, each of which is hereby incorporated by reference in its entirety.

STATEMENT REGARDING FEDERALLY SPONSORED RESEARCH OR DEVELOPMENT

Not Applicable

BACKGROUND OF THE INVENTION

Field of the Invention

The present invention generally relates to sleep monitors.

Description of the Related Art

Sleep monitors and bedroom environmental control do not currently exist as integrated systems and compete in separate marketplaces which serve similar markets. This product integrates the general output of any manner of sleep monitor systems in order to control and enhance any manner of bedroom environmental control systems.

There exist bedroom environment control systems, such as the Philips Hue smart light, Philips SmartSleep Wake-up Light, or Lutron lighting system, Hatch Restore, or any manner of timer-based oil diffusers. Additionally, there exist systems which monitor sleep state, analyze sleep patterns, and provide a user either real time sleep status such as with the Miku smart baby monitor, or post-processed sleep status such as the FitBit inspire HR.

These systems are not integrated.

BRIEF SUMMARY OF THE INVENTION

The present invention provides a system that is integrated in order to provide an automated control system for the user, which provides messaging to bedroom environmental control systems as a function of the status of the user's sleep state. This allows for control of lighting, sound, room scent, etc as a sleep aid, or for sleep therapy.

The present invention is a system and method for using any manner of sleep tracking system along with any manner of bedroom environmental control system or systems (light sources, sound machines, scent diffusers, etc) to aid a user in falling asleep and waking up.

One aspect of the present invention is a method for adjusting a bedroom environment control as a subject falls asleep and/or as the subject wakes up using a sleep monitoring system. The method includes monitoring the subject using a sleep monitoring system to detect at least one parameter, the at least one parameter comprising presence, motion, respiration rate, pulse rate or SpO2. The method also includes analyzing the at least one parameter for changes to determine the subject's sleep progression data. The method also includes transmitting the subject's sleep progression data to an interface for a bedroom environmental control system. The method also includes modifying a bedroom environment based on the subject's sleep progression data utilizing the bedroom environmental control system.

Another aspect of the present invention is a system for adjusting a bedroom environment control as a subject falls asleep and/or as the subject wakes up using a sleep monitoring sub-system. The system comprises a sleep monitoring sub-system and a bedroom environmental control sub-system. The sleep monitoring sub-system is configured to monitor the subject to detect at least one parameter, the at least one parameter comprising presence, motion, respiration rate, pulse rate or SpO2. The sleep monitoring sub-system is configured to analyze the at least one parameter for changes to determine the subject's sleep progression data. The sleep monitoring sub-system is configured to transmit the subject's sleep progression data to an interface for the bedroom environmental control system. The bedroom environmental control system is configured to modify a bedroom environment based on the subject's sleep progression data.

Yet another aspect of the present invention is a non-transitory computer-readable medium that stores a program that causes a processor to perform functions for adjusting a bedroom environment control as a subject falls asleep and/or as the subject wakes up using a sleep monitoring system by executing the following steps: monitoring the subject using a sleep monitoring system to detect at least one parameter, the at least one parameter comprising presence, motion, respiration rate, pulse rate or SpO2; analyzing the at least one parameter for changes to determine the subject's sleep progression data; transmitting the subject's sleep progression data to an interface for a bedroom environmental control system; and modifying a bedroom environment based on the subject's sleep progression data utilizing the bedroom environmental control system.

Having briefly described the present invention, the above and further objects, features and advantages thereof will be recognized by those skilled in the pertinent art from the following detailed description of the invention when taken in conjunction with the accompanying drawings.

BRIEF DESCRIPTION OF THE SEVERAL VIEWS OF THE DRAWINGS

FIG. 3. is a flow chart for a method for adjusting a bedroom environment control as a subject falls asleep and/or as the subject wakes up using a sleep monitoring system.

DETAILED DESCRIPTION OF THE INVENTION

Figure 1:
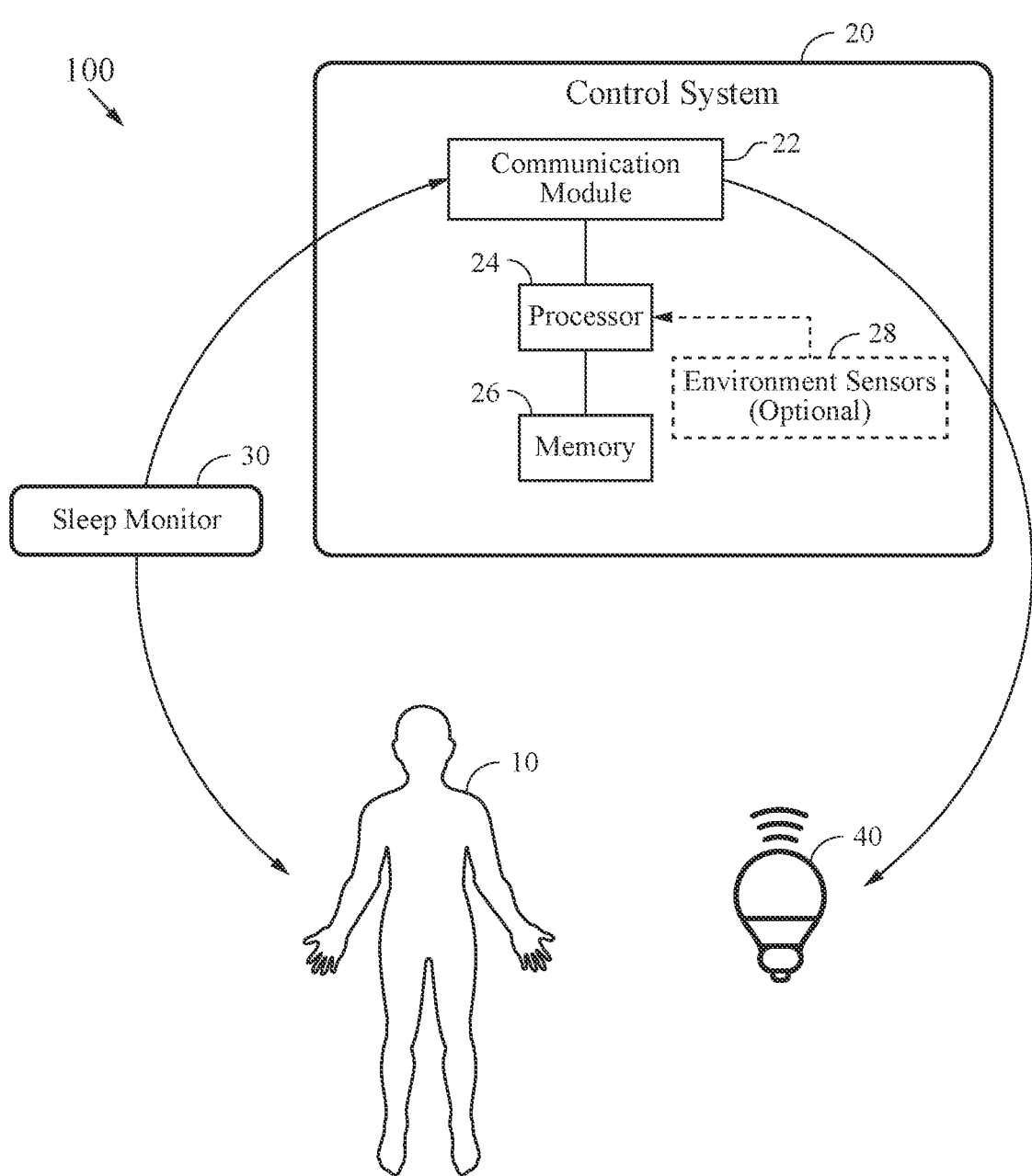
FIG. 1 is a block diagram of a system for adjusting a bedroom environment control as a subject falls asleep and/or as the subject wakes up using a sleep monitoring system.

A system which ingests sleep information such as presence and vitals detection from any manner of sleep monitoring, processes this data using an algorithm, and uses this to output control signals or messages to another system or systems which control the environmental conditions of a bedroom in order to enhance the sleep and wake experience of a user.

An algorithm ingests the output of a sleep monitor system such as the output of the MIKU smart baby monitor. This data may be provided via an API, through a direct connection such as bluetooth, or may be integrated within the system itself. The sleep system provides information such as presence, motion, and vitals such as respiration rate, pulse rate, and/or SpO2. This information is monitored, and tracked for changes which indicate this user's particular sleep progression such as entering different sleep stages.

An interface is then provided to the bedroom environmental control system such as to the Philips Hue lighting system. This interface may be provided via an API, through direct connection such as bluetooth, or may be integrated within the system itself. The system provides commands to the bedroom environmental control system such as "set lighting intensity to 25%" or "set lighting RGB to <255, 244, 229>."

Sensors such as light, temperature and sound sensors could provide positive feedback to a learning algorithm for enhanced system performance and insights to potential user actions such as the purchase of blackout curtains, white noise machines, or heating/cooling systems.

Sleep metrics could be correlated with bedroom environment conditions in order to inform the user as to conditions which enhance their sleep patterns, make automated adjustments, or show improvements to sleep patterns over time.

A preferred example of a bedtime routine algorithm is as follows: monitor sleep monitor output presence and vitals state every k minutes for N days (for example, k=1 minute, N=7 days); determine a bedtime b[n] and a sleep onset o[n] for each day n in N; compute a median bedtime and a sleep onset, b_median and o_median; for a given threshold b_median-o_median-T, configure light and sound for PRE_BED_STATE configuration state; T may be 20 minutes for example, and PRE_BED_STATE can be: {LIGHTS: 50% Intensity, SOUND: Cricket sounds}; Once bedtime has been observed, configure light and sound for ONSET_STATE, for example{LIGHTS: 0% Intensity, SOUND: White Noise}; Once sleep is observed, configure light and sound for SLEEP_STATE, for example{LIGHTS: 0% Intensity, SOUND: Silence}; and if it is observed the user wakes up during the night, WAKE_STATE can be configured for example{LIGHTS: 5% Intensity, SOUND: Silence}.

A preferred example of a wakeup routine algorithm is as follows: monitor sleep monitor output presence and vitals state every k minutes for N days (for example, k=1 minute, N=7 days); determine a waketime w[n] and a wake onset o[n] for each day n in N; compute a median bedtime and a sleep onset, b_median and o_median; For given threshold w_median-o_median-T, configure light and sound for PRE-_WAKE_STATE configuration state. T may be 20 minutes for example, and PRE_WAKE_STATE can be: {LIGHTS: 0% Intensity Sweep, SOUND: 0%}; Once wake onset has been observed, configure light and sound for WAKE_ON-SET_STATE, for example{LIGHTS: 0-100% Intensity Sweep, SOUND: 0-100% Volume Bird Chirp}; and Once it is observed the user is awake, configure light and sound for WAKE_STATE, for example{LIGHTS: 80% Intensity, SOUND: Light Music}.

A system 100 for adjusting a bedroom environment control as a subject 10 falls asleep and/or as the subject 10 wakes up using a sleep monitoring system 30 is shown in

4

FIG. 1. A communication module 22 of a control system 20 communicates with the sleep monitor 30, and communicates with the bedroom environmental control system 40. A processor 24 executes the algorithms. A memory 26 stores the information from the sensors. Optional environmental sensors 28 monitor the output of the environmental control system and improve algorithm performance.

Figure 2:
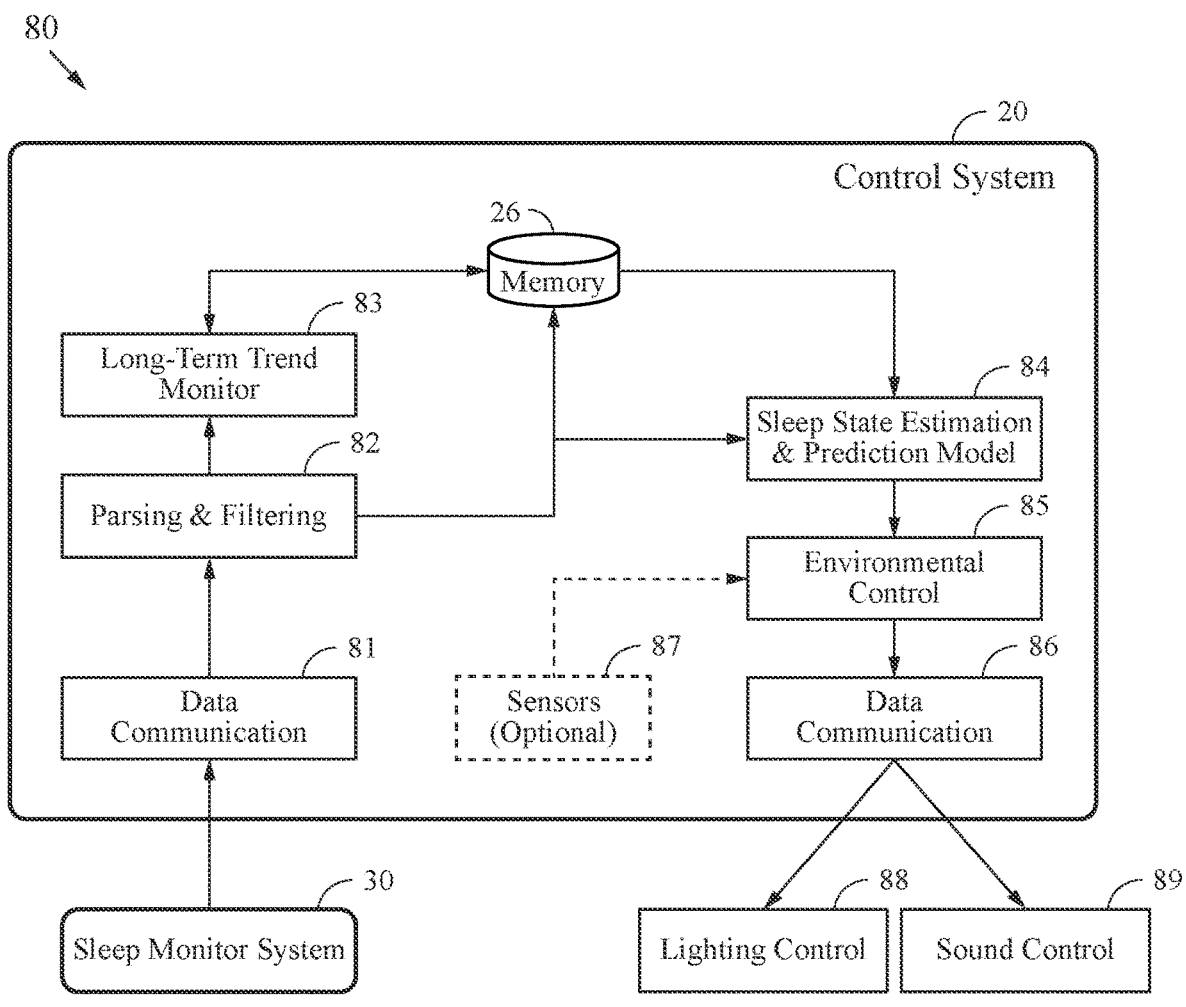
FIG. 2 is a block diagram of a system for adjusting a bedroom environment control as a subject falls asleep and/or as the subject wakes up using a sleep monitoring system.

FIG. 2 shows a process 80 of the system 100 for adjusting a bedroom environment control. The process includes the sleep monitor system 30 communicating data 81 to the control system 20. The process also includes parsing and filtering 82 the data, using a long-term trend monitor 83 and a sleep state estimation and prediction model 84, and storing the data in memory 26. The process also includes using the sleep state estimation and prediction model 84 for environmental control 85 which then communicates 86 with bedroom environmental controls such as a lighting control 88 and/or a sound control 89. Optionally, sensors 87 can monitor the output of the environmental control 85.

In one embodiment, the sleep monitoring sub-system comprises a RGB imaging sensor, a radar, a processor, and a user interface. The RGB imaging sensor is utilized to detect light reflected by a living subject from ambient or controlled light sources. The radar emits a radiofrequency at a specific frequency, and detects the frequency change of reflections of a plurality of targets which have subtle movements from the living subject. The processor is configured to run an algorithm to perform digital signal processing on data provided by the radar and the RGB sensor to generate presence and vitals information for the living subject for communication to the user interface.

In another embodiment, the sleep monitoring sub-system comprises a monitoring device and an interface device. The monitoring device comprises an IR imaging sensor, a radar, a processor, and a first communication module. The interface device comprises a second communication module and a user interface module. The IR imaging sensor is utilized to detect light reflected by a living subject from ambient or controlled light sources. The radar emits a radiofrequency at a specific frequency, and detects the frequency change of reflections of a plurality of targets which have subtle movements from the living subject. The processor is configured to run an algorithm to perform digital signal processing on data provided by the radar and the IR imaging sensor to generate presence and vitals information for the living subject for communication to the interface device.

In another embodiment, the sleep monitoring sub-system comprises an IR imaging sensor, a radar, a processor, and a user interface. The IR imaging sensor is utilized to detect light reflected by a living subject from ambient or controlled light sources. The radar emits a radiofrequency at a specific frequency, and detects the frequency change of reflections of a plurality of targets which have subtle movements from the living subject. The processor is configured to run an algorithm to perform digital signal processing on data provided by the radar and the IR sensor to generate presence and vitals information for the living subject for communication to the user interface.

Figure 4:
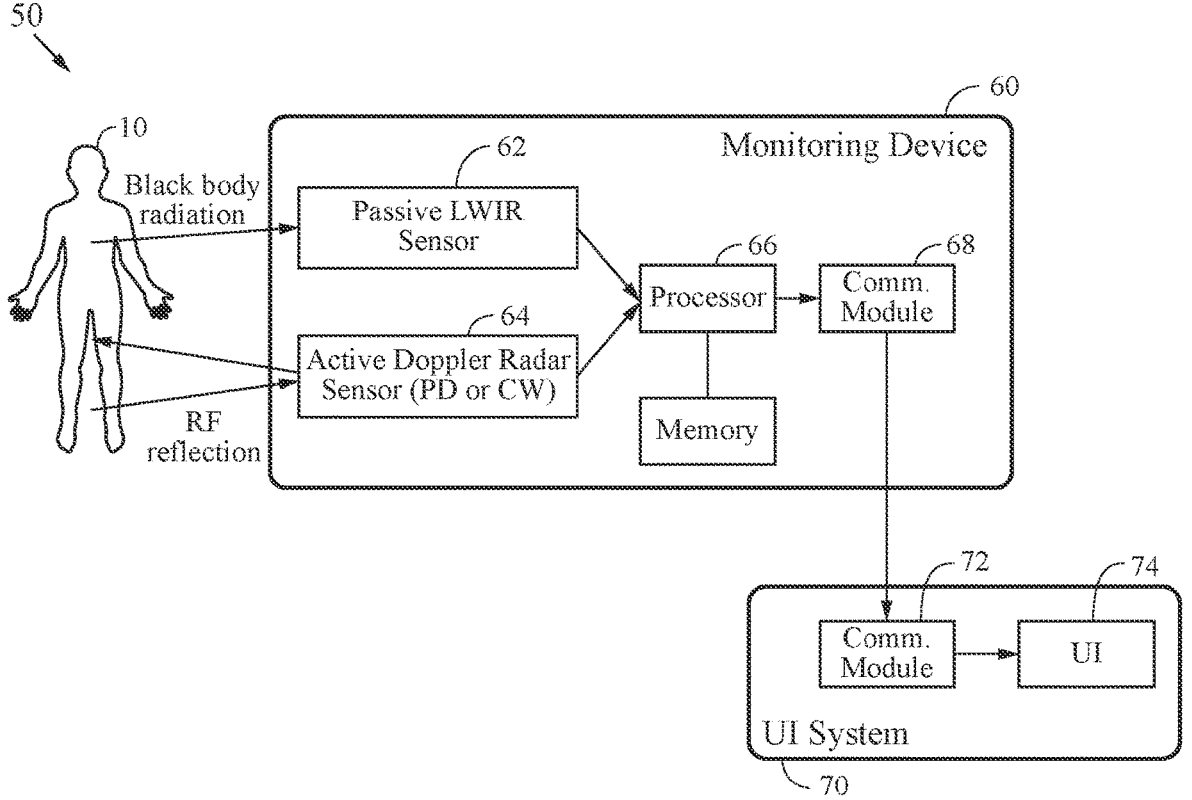
FIG. 4 is a block diagram of a sleep monitoring system.

In another embodiment, as shown in FIG. 4, the sleep monitoring sub-system 50 comprises a monitoring device 60 and an interface device 70. The monitoring device 60 comprises a passive long wave infrared ("LWIR") sensor 62, a radar 64, a processor 66, and a first communication module 68. The interface device 70 comprises a second communication module 72 and a user interface module 74. The LWIR sensor 62 is utilized to detect black-body radiation originating from a living subject 10. The radar 64 emits a radiofrequency at a specific frequency, and detects the frequency change of reflections of a plurality of targets which have subtle movements caused by the living subject 10. The processor 66 is configured to run an algorithm to perform digital signal processing on data provided by the radar 64 and the LWIR sensor 62 to generate presence and vitals information for the living subject 10 for communication to the interface device 70.

In another embodiment, the sleep monitoring sub-system comprises a passive long wave infrared ("LWIR") sensor, a radar, a processor, and a user interface. The LWIR sensor is utilized to detect black-body radiation originating from a living subject. The radar emits a radiofrequency at a specific frequency, and detects the frequency change of reflections of a plurality of targets which have subtle movements caused by the respiration and/or ballistocardiography from the living subject. The processor is configured to run an algorithm to perform digital signal processing on data provided by the radar and the LWIR sensor to generate presence and vitals information for the living subject for communication to the user interface.

In another embodiment, the sleep monitoring sub-system comprises a camera (such as a NANIT system), a processor, and a user interface.

In another embodiment, the sleep monitoring sub-system comprises a SpO2 monitor (such as an OWLET system), a processor, and a user interface.

A flow chart 90 for a method for adjusting a bedroom environment control as a subject falls asleep and/or as the subject wakes up using a sleep monitoring system is shown in FIG. 3. In step 91, a subject is monitored using a sleep monitoring system to detect at least one parameter. In step 92, the parameter is analyzed for changes to determine the subject's sleep progression data. In step 92, the sleep progression data is transmitted to an interface of a bedroom environment control system. Utilizing the bedroom environmental control system, the bedroom environment is modified based on the subject's sleep progression data in step 94.

Figure 5:
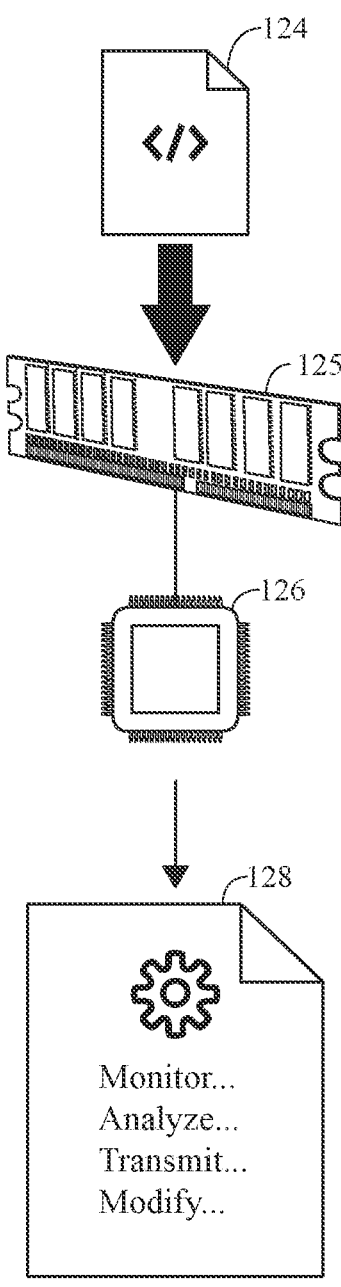
FIG. 5 is a block diagram of a non-transitory computer-readable medium of the present invention.

A non-transitory computer-readable medium 125 is shown in FIG. 5. A program 124 is stored in the non-transitory computer-readable medium 125 that causes a processor 126 to perform functions for adjusting a bedroom environment control by executing defined steps 128. The execution of the defined steps 128 includes monitoring the subject using a sleep monitoring system to detect at least one parameter, analyzing the at least one parameter for changes to determine the subject's sleep progression data, transmitting the subject's sleep progression data to an interface for a bedroom environmental control system, and modifying a bedroom environment based on the subject's sleep progression data utilizing the bedroom environmental control system.

The parameter preferably comprises presence, motion, respiration rate, pulse rate or SpO2.

White et al., U.S. patent Ser. No. 10/825,314 for a Baby Monitor, is hereby incorporated by reference in its entirety.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim.

Therefore, the embodiments of the invention in which an exclusive property or privilege is claimed are defined in the following appended claims.

We claim:

1. A method for adjusting a bedroom environment control as a subject falls asleep and/or as the subject wakes up using a sleep monitoring system, the method comprising:
   monitoring, via at least one non-contact sensor of a sleep monitoring system during a monitoring period, at least one real-time physiological parameter associated with the subject;
   utilizing at least one prediction model, based at least in part on-the at least one real-time physiological parameter, from throughout the monitoring period, and on historical sleep progression data from a long-term trend monitor, to forecast an impending transition of the subject entering into a particular sleep state within a future time window prior to an observed onset;
   preemptively initiating, responsive to the monitoring, in real-time, at least one environment change associated with promoting the impending transition into the particular sleep state; and
   transmitting, in real-time, over a network via at least one application programming interface (API), to at least one third-party network-connected bedroom environmental control device of a bedroom environmental control system, at least one control signal, the at least one control signal being configured to cause the at least one third-party network-connected bedroom environmental control device to modify at least one environmental condition of a bedroom environment based on the at least one environment change responsive to subject's sleep progression data and prior to the forecast transition, the at least one third-party network-connected bedroom environmental control device being independent from the sleep monitoring system.

2. The method according to claim 1 wherein the sleep monitoring system comprises:
   the at least one non-contact sensor;
   a radar;
   a processor; and
   a user interface;
      wherein the at least one non-contact sensor is utilized to detect black-body radiation originating from a subject;
      wherein the radar emits a radiofrequency at a specific frequency, and detects a frequency change of reflections of a plurality of targets which have subtle movements caused by respiration and/or a heart beat from the subject;
      wherein the processor is configured to run an algorithm to perform digital signal processing on data provided by the radar and the at least one non-contact sensor to generate presence and vitals information for the subject for communication to the user interface.

3. The method according to claim 1 wherein the sleep monitoring system comprises:
   a monitoring device comprising the at least one non-contact sensor, a radar, a processor, and a first communication module; and
   an interface device comprising a second communication module and a user interface module;
      wherein the at least one non-contact sensor is utilized to detect black-body radiation originating from a subject;
      wherein the radar emits a radiofrequency at a specific frequency, and detects a frequency change of reflections of a plurality of targets which have subtle movements caused by the subject;

wherein the processor is configured to run an algorithm to perform digital signal processing on data provided by the radar and the at least one non-contact sensor to generate presence and vitals information for the subject for communication to the interface device.

4. The method according to claim 1 wherein the bedroom environmental control system comprises a communication module, a processor, a memory, a long term trend monitor engine, a parsing and filtering engine, a sleep state estimation and prediction model, an environmental control engine, and a plurality of environment sensors.

5. The method according to claim 1 further comprising an application programming interface (API).

6. The method according to claim 1 wherein the at least one real-time physiological parameter comprises presence, motion, respiration rate, pulse rate or SpO2.

7. A system for adjusting a bedroom environment control as a subject falls asleep and/or as the subject wakes up using a sleep monitoring sub-system, the system comprising:

a sleep monitoring sub-system comprising at least one non-contact sensor; and wherein the sleep monitoring sub-system is configured to:

monitor, via at least one non-contact sensor of a sleep monitoring system during a monitoring period, at least one real-time physiological parameter associated with the subject;

utilize at least one prediction model, based at least in part on-the at least one real-time physiological parameter, from throughout the monitoring period, and on historical sleep progression data from a long-term trend monitor, to forecast an impending transition of the subject entering into a particular sleep state within a future time window prior to an observed onset;

preemptively initiate, responsive to the monitoring, in real-time, at least one environment change associated with promoting the impending transition into the particular sleep state; and transmit, in real-time, over a network via at least one application programming interface (API), to at least one third-party network-connected bedroom environmental control device of a bedroom environmental control system, at least one control signal, the at least one control signal being configured to cause the at least one third-party network-connected bedroom environmental control device to modify at least one environmental condition of a bedroom environment based on the at least one environment change responsive to subject's sleep progression data and prior to the forecast transition, the at least one third-party network-connected bedroom environmental control device being independent from the sleep monitoring system.

8. The system according to claim 7 wherein the sleep monitoring sub-system comprises:

the at least one non-contact sensor;

a radar;

a processor; and a user interface;

wherein the at least one non-contact sensor is utilized to detect black-body radiation originating from a subject;

wherein the radar emits a radiofrequency at a specific frequency, and detects a frequency change of reflections of a plurality of targets which have subtle movements caused by respiration and/or a heart beat from the subject;

wherein the processor is configured to run an algorithm to perform digital signal processing on data provided by the radar and the at least one non-contact sensor to generate presence and vitals information for the subject for communication to the user interface.

9. The system according to claim 7 wherein the sleep monitoring sub-system comprises:

a monitoring device comprising the at least one non-contact sensor, a radar, a processor, and a first communication module; and an interface device comprising a second communication module and a user interface module;

wherein the at least one non-contact sensor is utilized to detect black-body radiation originating from a subject;

wherein the radar emits a radiofrequency at a specific frequency, and detects a frequency change of reflections of a plurality of targets which have subtle movements caused by the subject;

wherein the processor is configured to run an algorithm to perform digital signal processing on data provided by the radar and the at least one non-contact sensor to generate presence and vitals information for the subject for communication to the interface device.

10. The system according to claim 7 wherein the bedroom environmental control sub-system comprises a communication module, a processor, a memory, a long term trend monitor engine, a parsing and filtering engine, a sleep state estimation and prediction model, an environmental control engine, and a plurality of environment sensors.

11. The system according to claim 7 further comprising an application programming interface (API).

12. The system according to claim 7 wherein the at least one real-time physiological parameter comprises presence, motion, respiration rate, pulse rate or SpO2.

\* \* \* \* \*